United States Patent [19]

Williams et al.

[11] 4,140,722
[45] * Feb. 20, 1979

[54] OXIDATION OF SUBSTITUTED p-XYLENES TO SUBSTITUTED TEREPHTHALALDEHYDES

[75] Inventors: James E. Williams; Kenneth E. Simmons, both of Kingsport, Tenn.

[73] Assignee: Eastman Kodak Company, Rochester, N.Y.

[ * ] Notice: The portion of the term of this patent subsequent to Apr. 12, 1994, has been disclaimed.

[21] Appl. No.: 779,432

[22] Filed: Mar. 21, 1977

Related U.S. Application Data

[63] Continuation-in-part of Ser. No. 611,381, Sep. 8, 1975, Pat. No. 4,017,547.

[51] Int. Cl.$^2$ .............................................. C07C 45/02
[52] U.S. Cl. ................................ 260/599; 260/600 R
[58] Field of Search ................................ 260/599, 600

[56] References Cited

U.S. PATENT DOCUMENTS

| | | | |
|---|---|---|---|
| 3,597,485 | 8/1971 | Brill | 260/599 |
| 3,845,137 | 10/1974 | Magder | 260/599 |
| 4,017,547 | 4/1977 | Simmons et al. | 260/599 |

*Primary Examiner*—Bernard Helfin
*Attorney, Agent, or Firm*—Edward R. Weber; Daniel B. Reece, III

[57] ABSTRACT

Substituted terephthalaldehydes are produced by the vapor phase oxidation of similarly substituted p-xylenes in the presence of a catalyst mixture of tungsten in the form of an oxide or silicotungstic acid, molybdenum in the form of an oxide and optionally bismuth in the form of an oxide.

17 Claims, No Drawings

OXIDATION OF SUBSTITUTED P-XYLENES TO SUBSTITUTED TEREPHTHALALDEHYDES

This application is a continuation-in-part of U.S. Application Ser. No. 611,381, filed Sept. 8, 1975 and now U.S. Pat. No. 4,017,547.

This invention concerns an improved process for the vapor phase oxidation of substituted p-xylenes to similarly substituted terephthalaldehydes.

U.S. Pat. No. 3,597,485 discloses that triformyl benzene is selectively produced in high yield when pseudocumene is subjected to a vapor-phase oxidation in the presence of a catalyst mixture consisting of oxides of tungsten and molybdenum.

U.S. Pat. No. 3,845,137 claims a process for preparation of a polyfunctional aromatic aldehyde in which an alkylbenzene is oxidized in the vapor phase in the presence of a supported catalyst mixture of oxides of tungsten and molybdenum and at least one third metal or oxide selected from the group consisting of calcium, barium, titanium, zirconium, hafnium, thallium, niobium, zinc, and tin. The initial surface area of the catalyst is between 2 square meters per gram and 10 square meters per gram. The indicated advantage over the basic patent (U.S. Pat. No. 3,597,485) achieved by using the three-component system is an improvement in catalyst life. This art also teaches that triformyl benzene is produced by vapor-phase oxidation of pseudocumene.

We have discovered that methyl terephthalaldehyde, not triformyl benzene as claimed in the prior art, is the primary product from the oxidation of pseudocumene. Indeed, it has been shown that meta or ortho xylenes are not converted to the corresponding dialdehydes by the oxidation procedure of this invention. Only when there are two methyl groups in the 1,4-positions does a dialdehyde result from the oxidation. Dialdehydes result from oxidation of compounds of the following formula:

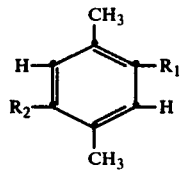

where $R_1$ is lower alkyl of 1 to 3 carbon atoms, lower alkoxy, or hydroxy and $R_2$ is hydrogen, lower alkyl of 1 to 3 carbon atoms, lower alkoxy or hydroxy. Substituted terephthalaldehydes are obtained both with a catalyst consisting of oxides of tungsten and molybdenum, and with a catalyst containing molybdenum and bismuth, in the form of oxides, and tungsten, either as the oxide or in the form of silicotungstic acid.

We have also discovered that the conversion of substituted p-xylene to substituted terephthalaldehyde is improved substantially by the addition to the catalyst composition of a catalytically effective amount of an oxide of bismuth. Not only is the conversion increased substantially by the use of an oxide of bismuth, but catalyst life is improved considerably, thereby permitting the operation of the oxidation process for much longer periods of time before the reaction must be recharged with fresh catalyst. These two primary advantages are of utmost importance for the operation of the oxidation process continuously on a commercial scale.

The catalyst composition used in one improved process is a mixture of tungsten, bismuth and molybdenum in an atom ratio of between about 5:0.1:1 and 20:2:1, the preferred ratio being about 10:1:1. The catalyst mixture preferably is deposited on a suitable catalyst support such as, for example, low surface area alumina, silica or silicon carbide which is the preferred support. The support preferably has a surface area of about 0.01 to 1 m.$^2$/g. with about 0.1 to 0.5 m.$^2$/g. being especially preferred. The weight percent of the tungsten, bismuth and molybdenum on the support can be in the range of about 5 to 10. The catalyst composition therefore consists essentially of tungsten as an oxide or silicotungstic acid, molybdenum as an oxide and bismuth as an oxide as the catalytic ingredients.

The catalysts used in the novel process of our invention are prepared according to known techniques. Typically, aqueous solutions of water-soluble compounds containing tungsten, bismuth and molybdenum are mixed in a manner to give a tungsten to bismuth to molybdenum atom ratio of between about 5:0.1:1 and 20:2:1. A suitable carrier is added to the resulting solution and the solution is evaporated while the support is mixed thoroughly with the solution. The dried catalyst then is calcined, for example, by heating at about 250° C. for about 2 hours and at 500° C. for 2 hours. Examples of the water-soluble compounds which can be used in preparing the catalysts include ammonium paratungstate, ammonium metatungstate, silicotungstic acid, ammonium molybdate, silicomolybdic acid, phosphomolybdic acid and bismuth nitrate.

The reaction temperature used in our improved process should be sufficiently high so that a desirable rate of oxidation occurs, but not so high as to cause undesirable side reactions. Thus, temperatures in the range of 500° C. to 600° C., preferably 520° C. to 580° C., may be employed. Atmospheric pressure may be used, but both moderately elevated or reduced pressures may be employed if desired.

The contact times of reactants with the catalyst may be between 0.01 and 1 second with the preferred contact time being about 0.1 to 0.2 second. Although the air to substituted p-xylene mole ratio may be varied widely, for example, between about 100:1 to 200:1, we prefer a ratio in the range of about 125:1 to 175:1.

Our improved process utilizing the novel catalyst composition described above is further illustrated by the following examples.

Oxidations in the following examples were carried out at a reaction temperature of 520°–580° C. and atmospheric pressure with a contact time of 0.2 second.

$$\text{calculated at reaction temperature and pressure)} \over \text{bulk volumes of catalyst, ml.}$$
(ml. of total feed per second In a typical instance, 1 mole of substituted p-xylene was fed to the reactor for every 172 moles of air fed. Conversions and yields of substituted terephthalaldehyde were based on quantitative gas chromatographic analyses of solutions of the reaction products.

The terms conversion and yield are defined by the following expressions:

% Conversion to substituted terephthalaldehyde =
$$\frac{\text{moles of substituted terephthalaldehyde produced} \times 100}{\text{moles of substituted p-xylene fed}}$$

% Yield of substituted terephthaladehyde =

-continued $$\frac{\text{moles of substituted terephthalaldehyde produced} \times 100}{\text{moles of substituted p-xylene consumed.}}$$

The invention will be further illustrated by the following examples, although it will be understood that these examples are included merely for purposes of illustration and are not intended to limit the scope of the invention.

EXAMPLE 1

A catalyst composition of 0.5% $MoO_3$ + 1% $Bi_2O_3$ + 8.5% $WO_3$ on silicon carbide is prepared as follows. Ammonium molybdate (0.68 gram) and ammonium metatungstate (11.21 grams) are dissolved in approximately 40 milliliters of water. Bismuth nitrate [$Bi(NO_3)_3 \cdot 5H_2O$, 2.31 grams] is dissolved in approximately 50 milliliters of dilute nitric acid. These solutions are combined and mixed with 100 grams of silicon carbide support (Carborundum Company Type CHO, 8 × 20 mesh granules). Drying is accomplished on a steam bath with manual stirring. Further drying is done in a vacuum oven at 125° C. and 20 inch Hg vacuum for 2 hours. The catalyst is then calcined at 250° C. (2 hours) and at 500° C. (2 hours). The oxidation is carried out in a tubular reactor made of Vycor glass, 25 millimeters outer diameter and 19 inches long heated by a single-element electric furnace. The reactor is charged with approximately 10 milliliters of catalyst. Pseudocumene is oxidized over this catalyst by feeding air at approximately 943 milliliters/minute STP, and liquid pseudocumene at approximately 0.031 milliliters/minute. The product collection apparatus consists of a 1-liter, three-necked flask followed by a Vigreux column 2 feet long.

The reactor is operated for a period of 6 hours during which time a quantity of 10.5 grams of pseudocumene is fed. Reaction temperature is approximately 580° C. The solid product is dissolved in methyl acetate and separated from the water layer. The methyl acetate is evaporated and the identity of the resulting solid is confirmed as methyl terephthalaldehyde by NMR analysis.

EXAMPLE 2

A 0.6% $MoO_3$ + 9.7% $WO_3$ on silicon carbide catalyst is prepared by dissolving 0.96 gram ammonium molybdate and 13 grams ammonium paratungstate in water and combining these solutions with 100 grams of silicon carbide catalyst support. The catalyst is dried at 110° C., 20 in Hg vacuum and calcined 3 hours at 540° C. The reactor is a 3-foot long, 1-inch diameter Vycor glass tube which is heated by a three-element tubular electric furnace. The reactor is charged with approximately 35 milliliters of catalyst. Pseudocumene is oxidized over this catalyst by feeding air at approximately 3.3 liters/minute STP, and liquid pseudocumene at approximately 0.12 milliliters/minute. The product collection apparatus consists of a 2-inch diameter, air-cooled U-tube which is 10 inches long, and a Vigreux column 2 feet long. Downstream, unreacted pseudocumene is collected in two traps which are cooled with dry ice in n-butyl alcohol.

The reactor is operated for two hours during which time a quantity of 12.6 grams (0.105 mole) of pseudocumene is fed. The reaction temperature is approximately 520° C. The solid which is collected in the U-tube and Vigreux column is dissolved in acetone and analyzed by gas chromatography. Analysis indicates that the solution contains 3.85 grams (0.026 mole) of methyl terephthalaldehyde along with minor concentrations of several by-products. Analysis of the material collected in the traps indicates that 7.56 grams (0.063 mole) of pseudocumene is recovered. Hence, the conversion of pseudocumene to methyl terephthalaldehyde is 25% and the yield is 62%.

EXAMPLE 3

A catalyst composition of 0.5% $MoO_3$ + 1% $Bi_2O_3$ + 10% silicotungstic acid on silicon carbide is prepared as follows: ammonium molybdate (0.69 gram) and silicotungstic acid (11.3 grams) are dissolved in approximately 40 milliliters of water. Bismuth nitrate [$Bi(NO_3)_3 \cdot 5H_2O$, 2.35 grams] is dissolved in approximately 50 milliliters of dilute nitric acid. These solutions are mixed and combined with 100 grams of silicon carbide support (Carborundum Company Type CHO, 8 × 20 mesh granules). Drying is accomplished on a steam bath with manual stirring. Further drying is done in a vacuum oven at 125° C., followed by calcination at 250° C. (2 hours) and 500° C. (2 hours). This catalyst is used to oxidize pseudocumene in the same manner as in Example 2. The reactor is operated for a period of 2 hours during which time a quantity of 12.6 grams of pseudocumene is fed at a reaction temperature of approximately 520° C. Analysis of the acetone solution of product indicates that it contains 5.18 grams (0.035 moles) of methyl terephthalaldehyde and unidentified by-products in minor concentrations. Analysis of the material in the traps indicates that it contains 7.92 grams of pseudocumene. The conversion of pseudocumene to methyl terephthalaldehyde is 33%, with a yield of 90%.

The following comparative examples demonstrate that alkyl groups are converted to aldehyde groups only when they are in the 1,4-positions on the aromatic ring.

EXAMPLE A

A catalyst composition of 0.5% $MoO_3$ + 1% $Bi_2O_3$ + 8.5% $WO_3$ on silicon carbide is prepared in the same manner as in Example 1. The tubular reactor is charged with approximately 10 milliliters of catalyst. Liquid o-xylene is fed at approximately 0.031 milliliters per minute, and air at approximately 943 milliliters per minute. The reactor is operated for a period of 6 hours during which time a quantity of 10.1 grams of o-xylene is fed. Reaction temperature is approximately 565° C. Little reaction apparently occurs. A small amount of brown oil, probably o-tolualdehyde, is the only material in the product collector. No solid is found in either the product collector or the traps.

EXAMPLE B

The catalyst of the previous example (0.5% $MoO_3$ + 1% $Bi_2O_3$, + 8.5% $WO_3$ on silicon carbide) is used in the oxidation of m-xylene. Using a 10 milliliter catalyst charge, liquid m-xylene is fed at approximately 0.063 milliliters per minute and air at approximately 1880 milliliters per minute. The reactor is operated for a period of 6 hours during which time a quantity of 19.2 grams of m-xylene is fed. Reaction temperature is approximately 550° C. Gas chromatographic analysis of the liquid material in the product collector and the traps indicates that it is a mixture of unreacted m-xylene and m-tolualdehyde.

Substituted terephthaldehydes produced by this process are known chemicals having various known uses. For example, methyl terephthalaldehyde produced by the process of this invention is useful in preparation of specialty chemicals, dyes, and the like. It can be reduced to the corresponding methyl-substituted glycol, which has utility as a polymer intermediate.

Although the invention has been described in considerable detail with particular reference to certain preferred embodiments thereof, variations and modifications can be effected within the spirit and scope of the invention.

We claim:

1. In a process for preparing a dialdehyde of the formula

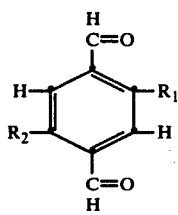

by the vapor phase oxidation of a compound of the formula

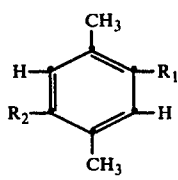

wherein $R_1$ is lower alkyl of 1 to 3 carbon atoms, lower alkoxy, or hydroxy, and $R_2$ is hydrogen, lower alkyl of 1 to 3 carbon atoms, lower alkoxy or hydroxy, in the presence of a supported catalyst mixture of molybdenum in the form of an oxide and tungsten in the form of an oxide or silicotungstic acid, the improvement which comprises employing an oxide of bismuth on the supported catalyst.

2. The process of claim 1 wherein the bismuth to molybdenum atom ratio is about 0.1:1 to 2:1.

3. The process of claim 1 wherein the tungsten to bismuth to molybdenum atom ratio is about 5:0.1:1 to 20:2:1.

4. The process of claim 1 wherein $R_1$ is alkyl of 1 to 3 carbon atoms and $R_2$ is hydrogen or alkyl of 1 to 3 carbon atoms.

5. A process for the preparation of a dialdehyde of the formula

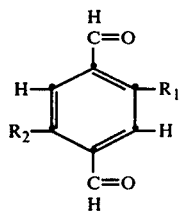

which comprises contacting a mixture of a compound of the formula

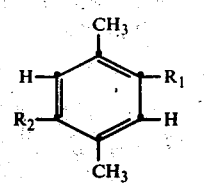

where $R_1$ is lower alkyl of 1 to 3 carbon atoms, lower alkoxy, or hydroxy, and $R_2$ is hydrogen, lower alkyl of 1 to 3 carbon atoms, lower alkoxy, or hydroxy, and an oxygen-containing gas with a supported catalyst mixture of tungsten in the form of an oxide or silicotungstic acid, molybdenum in the form of an oxide and bismuth in the form of an oxide at a temperature of about 500° C. to about 600° C.

6. The process of claim 5 in which the mixture is contacted with the catalyst for about 0.01 to 1 second and the tungsten to bismuth to molybdenum atom ratio is about 5:0.1:1 to 20:2:1.

7. The process of claim 5 wherein $R_1$ is alkyl of 1 to 3 carbon atoms and $R_2$ is hydrogen or alkyl of 1 to 3 carbon atoms.

8. A process for the preparation of a dialdehyde of the formula

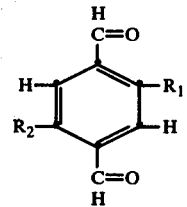

which comprises contacting for about 0.1 to 0.2 second a mixture of a compound of the formula

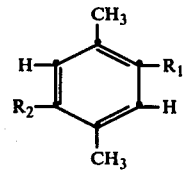

where $R_1$ is lower alkyl of 1 to 3 carbon atoms, lower alkoxy, or hydroxy, and $R_2$ is hydrogen, lower alkyl of 1 to 3 carbon atoms, lower alkoxy, or hydroxy, and air in a reactant to air mole ratio of about 1:100 to 1:200 with a supported catalyst mixture of tungsten in the form of an oxide or silicotungstic acid, molybdenum in the form of an oxide and bismuth in the form of an oxide at a temperature of about 520° C. to 580° C., wherein the tungsten to bismuth to molybdenum atom ratio is about 10:1:1 and the support has a surface area of about 0.01 to 1.0 square meters per gram.

9. The process of claim 8 wherein the contact time is about 0.2 second, the reactant to air mole ratio is about 1:172, the temperature is about 550° C. and the support has a surface area of about 0.1 to 0.5 square meters per gram.

10. The process of claim 8 wherein $R_1$ is alkyl of 1 to 3 carbon atoms and $R_2$ is hydrogen or alkyl of 1 to 3 carbon atoms.

11. In a process for preparing methyl terephthalaldehyde by the vapor phase oxidation of pseudocumene in the presence of a supported catalyst mixture of molybdenum in the form of an oxide and tungsten in the form of an oxide or silicotungstic acid, the improvement which comprises employing an oxide of bismuth on the supported catalyst.

12. The process of claim 11 wherein the bismuth to molybdenum atom ratio is about 0.1:1 to 2:1.

13. The process of claim 11 wherein the tungsten to bismuth to molybdenum atom ratio is about 5:0.1:1 to 20:2:1.

14. A process for the preparation of methyl terephthalaldehyde which comprises contacting a mixture of pseudocumene and an oxygen-containing gas with a supported catalyst mixture of tungsten in the form of an oxide or silicotungstic acid, molybdenum in the form of an oxide and bismuth in the form of an oxide at a temperature of about 500° C. to 600° C.

15. The process of claim 14 in which the mixture is contacted with the catalyst for about 0.01 to 1 second and the tungsten to bismuth to molybdenum atom ratio is about 5:0.1:1 to 20:2:1.

16. A process for the preparation of methyl terephthalaldehyde which comprises contacting for about 0.1 to 0.2 second a mixture of pseudocumene and air in a pseudocumene to air mole ratio of about 1:100 to 1:200 with a supported catalyst mixture of tungsten in the form of an oxide or silicotungstic acid, molybdenum in the form of an oxide and bismuth in the form of an oxide at a temperature of about 520° C. to 580° C., wherein the tungsten to bismuth to molybdenum atom ratio is about 10:1:1 and the support has a surface are of about 0.01 to 1.0 square meters per gram.

17. The process of claim 16 wherein the contact time is about 0.2 second, the pseudocumene to air mole ratio is about 1:172, the temperature is about 550° C., and the support has a surface area of about 0.1 to 0.5 square meters per gram.

* * * * *